US010898434B2

(12) United States Patent
Naumov

(10) Patent No.: US 10,898,434 B2
(45) Date of Patent: Jan. 26, 2021

(54) SINGLE-WALLED CARBON NANOTUBE-ASSISTED ANTIBIOTIC DELIVERY AND IMAGING TECHNIQUES

(71) Applicant: Texas Christian University, Fort Worth, TX (US)

(72) Inventor: Anton V. Naumov, Arlington, TX (US)

(73) Assignee: Texas Christian University, Fort Worth, TX (US)

( * ) Notice: Subject to any disclaimer, the term of this patent is extended or adjusted under 35 U.S.C. 154(b) by 0 days.

(21) Appl. No.: 16/366,007

(22) Filed: Mar. 27, 2019

(65) Prior Publication Data

US 2019/0343765 A1 Nov. 14, 2019

Related U.S. Application Data

(60) Provisional application No. 62/670,949, filed on May 14, 2018.

(51) Int. Cl.
| | |
|---|---|
| *A61K 31/65* | (2006.01) |
| *A61K 9/00* | (2006.01) |
| *A61P 31/04* | (2006.01) |
| *A61K 31/43* | (2006.01) |
| *B82Y 5/00* | (2011.01) |

(52) U.S. Cl.
CPC ............ *A61K 9/0092* (2013.01); *A61K 31/43* (2013.01); *A61K 31/65* (2013.01); *A61P 31/04* (2018.01); *B82Y 5/00* (2013.01)

(58) Field of Classification Search
CPC ...... A61K 9/0092; A61K 31/65; A61K 31/04; A61K 31/43; B82Y 5/00
See application file for complete search history.

(56) References Cited

U.S. PATENT DOCUMENTS 6,451,339 B2 * 9/2002 Patel .................... A61K 9/4858
424/451

FOREIGN PATENT DOCUMENTS

CA 2957805 A1 * 2/2016 ............. A61K 31/05

OTHER PUBLICATIONS

Antoszczak et al., Synthesis, antiproliferative and antibacterial activity of new amides of salinomycin, Feb. 25, 2014, Bioorganic & Medicinal Chemistry Letters, vol. 24, pp. 1724-1729. (Year: 2014).*
Assali, M. et al.; "Single-Walled Carbon Nanotubes-Ciprofloxacin Nanoantibiotic: Strategy to Improve Ciprofloxacin Antibacterial Activity" International Journel of Nanomedicine. 201: 12, 6647-6659 http://dx.doi.org/10.2147/IJN.S40625.
Li, H., et al.; "Adsorption of Antibiotic Ciprofloxacin on Carbon Nanotubes: Ph Dependence and Thermodynamics"; Chemosphere 95, 150-155; copyright 2013 http://dx.doi.org/10.1016/j.chemosphere.2013.08.053.
Bashiz, R. T., et al.; "Carbon Nanotubes as the Specific Drug Delivery for Sulfonamides Antibiotics: Instead of Injection"; Journal of Computational and Theoretical Nanoscience 12, 3 pages, doi:10.1166/jctn.2015.4286; copyright Oct. 2015.
Wu, W. et al.; "Targeted Delivery of Amphotericin B to Cells by Using Functionalized Carbon Nanotubes"; Angewandte Chemie International Edition 44, 6358-6362, doi:10.1002/anie.200501613 (2005).Wu, W. et al. Targeted Delivery of Amphotericin B to Cells by Using Functionalized Carbon Nanotubes, Angewandte Chemie International Edition 44, 6358-6362, doi:10.1002/anie.200501613; copyright 2005.
Prajapati, V. K. et al.; "An oral formulation of amphotericin B attached to functionalized carbon nanotubes is an effective treatment for experimental visceral leishmaniasis"; Journal of Infectious Diseases 205, 333-336; copyright 2011.

* cited by examiner

*Primary Examiner* — Ali Soroush
(74) *Attorney, Agent, or Firm* — Whitaker Chalk Swindle & Schwartz PLLC; Charles Gunter

(57) ABSTRACT

A new route is shown for at delivery in fighting drug resistant infections. Nanotubes and antibiotics and complexed non-covalently, with no chemical bonding, but through adsorption of antibiotics onto the nanotube surface governed by sufficiently strong molecular attraction between hydrophobic systems of the two. This allows the antibiotics to be freed from the nanotubes more easily as they reach the cell membrane. When antibiotics are introduced with nanotubes in this manner, bacterial resistance is mitigated by nanotube transport potentially into the membrane of the bacteria. Nanotubes used in this way help to overcome antibiotic resistance.

9 Claims, 12 Drawing Sheets

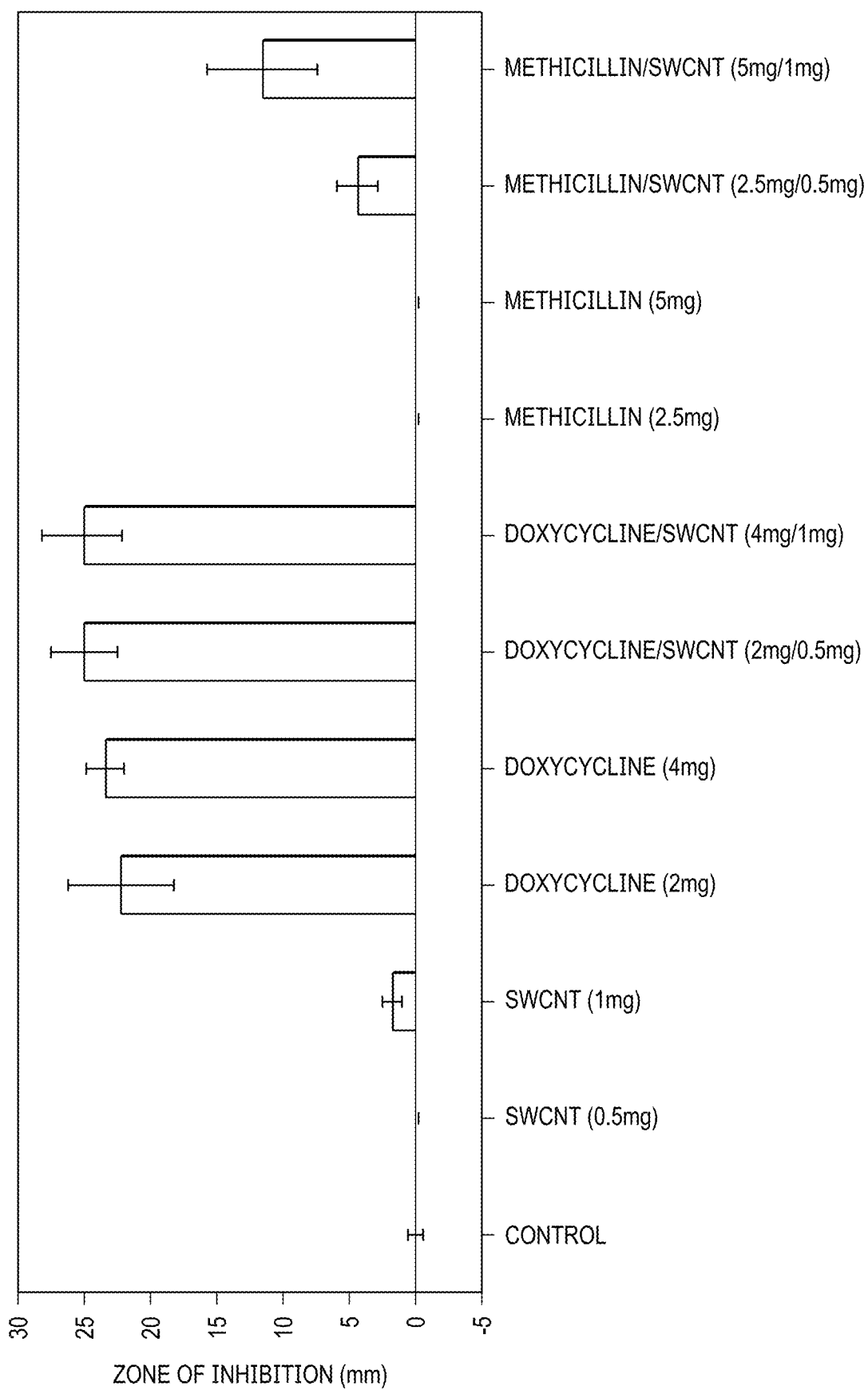

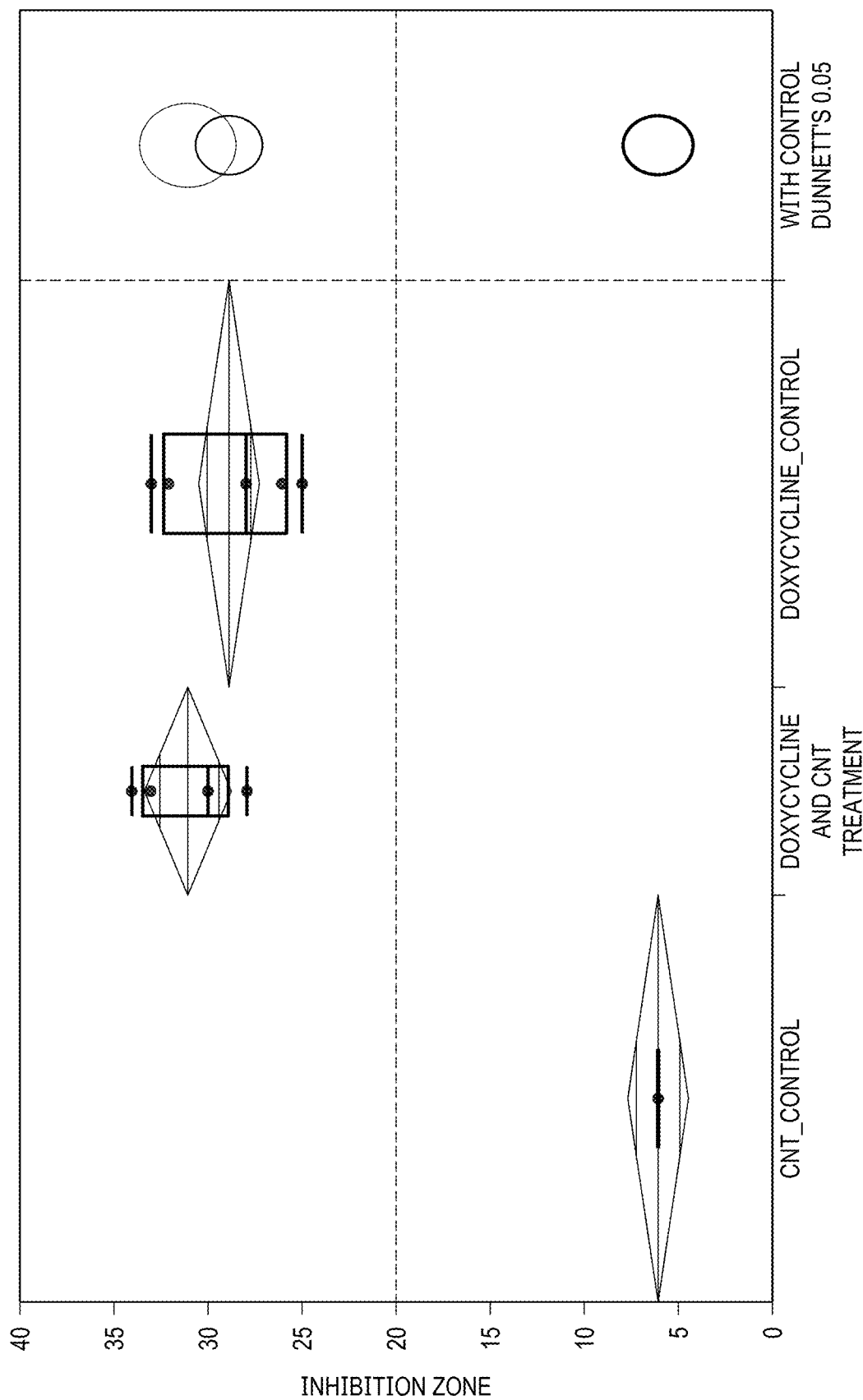

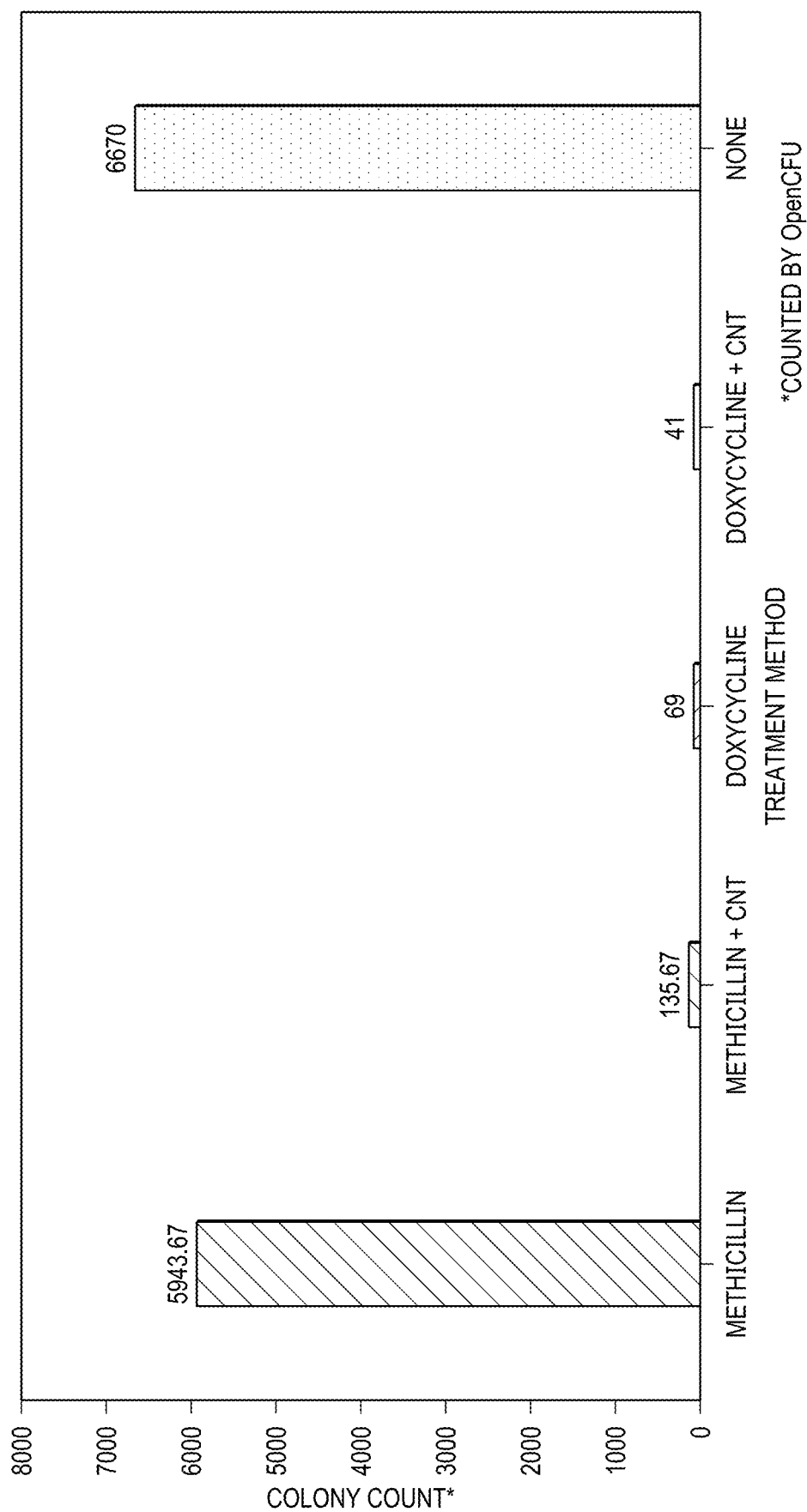

SINGLE-WALLED CARBON NANOTUBE-ASSISTED ANTIBIOTIC DELIVERY AND IMAGING TECHNIQUES

CROSS-REFERENCE TO RELATED APPLICATION

The present application claims priority to U.S. Provisional Patent Application Ser. No. 62/670,949 filed May 14, 2018, by the same inventor and with the same title.

BACKGROUND OF THE INVENTION

1. Field of the Invention

The present invention relates generally to the field of carbon nanotubes and to methods for using these nanotubes in therapeutic antibiotic delivery systems and in circumventing antibiotic resistance.

2. Description of the Prior Art

Infectious disease remains one of the leading causes of death worldwide. Although antibiotics revolutionized medicine in the $20^{th}$ century, overuse and misuse during the past 50 years has allowed for rapid emergence of drug resistance among numerous pathogens. In turn, there has been a tremendous decline in treatment efficacy for common infections as well as an increase in severe opportunistic infections caused by bacteria that now have resistance to multiple antibiotics. Multidrug resistant (MDR) bacteria including *Staphylococcus aureus, E. coli, Pseudomonas aeruginosa,* and *Klebsiella pneumonia* pose an ever-increasing threat as they are associated with severe nosocomial infections in healthcare settings, and, more recently, have gained prominence as the causative agents of community-acquired infections. In addition to the aforementioned bacteria, *Staphylococcus epidermidis* has gained prominence as an MDR, opportunistic pathogen. This bacterium has historically been viewed as being a harmless, commensal species but recent evidence suggests that its role in neonatal morbidity has been grossly underestimated. Furthermore, it has become one of the most common causative agents of nosocomial infections. To date, MDR pathogens have exhibited resistance towards all existing classes of antibiotics. Escalating drug resistance has been facilitated by the ease of transmission of resistance genes among different types of bacteria tier several types of antibiotics, further underscoring the need to address this global health crisis. Without significant advancements to current standards of care, it is estimated that antibiotic-resistant bacterial infections will become the leading cause of death by 2050, outpacing cancer-related deaths worldwide.

Significant efforts are underway in order to thwart mounting drug resistance. As an example, the development of inhibitory compounds to disable efflux pumps are a major focus. Efflux pumps are used by bacteria to bind to and pump antibiotics out of the bacterial cell, thereby minimizing the intracellular concentration of drugs and rendering them ineffective. However, toxic side effects have prevented efflux pump inhibitors from being brought to the clinic to date. Separately, there is tremendous focus on developing methods in order to stimulate immune-mediated clearance of pathogens (and cancer cells). It is thought that immunotherapeutics will offer enhanced treatment efficacy while also minimizing the risk for adverse side effects. Moreover, by targeting host molecules as opposed to bacterial targets, immunotherapeutics would mitigate developing, drug resistance. Additionally, there is significant emphasis on the use of antibiotic potentiators in order to restore efficacy for existing drug compounds.

In spite of the above areas in which advances have been made, a need exists for drug delivery systems which would allow for more effective drug delivery and uptake, thereby overcoming limitations with existing drug therapies.

SUMMARY OF THE INVENTION

The present invention involves the use of single-walled carbon nanotubes (SWCNTs) complexed to antibiotics to facilitate delivery and uptake, imaging, and enhanced antibacterial activity. To date, the use of SWCNTs complexed with different antibiotics has been demonstrated to show the increased antibacterial activity against drug-resistant *Staphylococcus epidermidis*. The proposed use of SWCNTs, as described herein, in combination with existing antibiotics, could allow for enhanced delivery and drug efficacy, while also allowing for fluorescence-based tracking of transported therapeutics.

The improved systems and techniques of the invention thus involve a particular type of antibiotic delivery system which is based upon single-walled carbon nanotubes (SWCNTs). It is known that the characteristics of SWCNTs indicate that they are well suited for cellular internalization, exhibit low cytotoxicity when formulated with drug compounds, and, that a significant amount of SWCNTs can be loaded onto a target cell. Collectively, these characteristics make SWCNTs ideally suited for drug delivery. As an added benefit, it is indicated that SWCNTs can be used for fluorescence imaging to track the location of drug therapeutics in cells and tissues with low background interference.

Given these features, the present invention deals with the development of improved antibiotic delivery systems of the type comprised of SWCNTs complexed with antibiotics. In the case of the present invention, the SWCNTs were non-covalently complexed with doxycycline and methicillin in separate experiments and dispersed in water. In each case, SWCNTs with antibiotics attached to their surface correlated with enhanced antibacterial activity against *Staphylococcus epidermidis*. Multiple sensitivity assays were performed to confirm enhanced antibacterial efficacy by the SWCNTs complexed with antibiotics. Notably, the results show a 68% increase in bacterial colony inhibition for SWCNT/doxycyclinc and 40-fold improvement in bacterial colony inhibition for *SWCNT/methicillin, in which *S. epidermidis* is initially resistant to methicillin. These findings support the ability of SWCNTs to serve as effective antibiotic delivery systems for multiples types of drugs. Moreover, the invention demonstrates the potential to bypass antibiotic drug resistance using SWCNT/methicillin.

Another aspect of the invention concerns the fact that it was also possible to visualize SWCNT fluorescent imaging inside *S. epidermidis* bacterial cells, thus demonstrating the ability to use SWCNTs as an imaging tool to track drug delivery. The fluorescence imaging data support the potential use of this as a powerful research tool for drug delivery and uptake, allowing further elucidation of antibiotic resistance mechanisms.

As described herein, the systems and techniques of the invention present a SWCNT antibiotic delivery system with demonstrated antibacterial activity against *Staphylococcus epidermidis* using SWCNT/doxycycline and SWCNT/methicillin. As will be described in detail, the methods of the invention have confirmed utility for two different classes of antibiotics and quite notably, have shown efficacy in cells that are initially resistant to methicillin, thereby suggesting an ability to bypass drug resistance via SWCNT-mediated delivery of methicillin directly into the bacterial cells. Significantly, in the method of the present invention, nanotubes and antibiotics are complexed non-covalently, with no chemical bonding, but through adsorption of antibiotics on the nanotube surface being governed by sufficiently strong molecular attraction between hydrophobic systems of the two. This technique allows antibiotics to get off the nanotubes easier as they reach cell membrane. Otherwise water insoluble nanotubes are dispersed by antibiotics themselves.

Work was done with bacterial strains that, according to the experiments described herein, show resistance to antibiotics without nanotubes. When antibiotics are introduced with nanotubes, that resistance is mitigated by nanotube transport potentially into the membrane of bacteria. The strains of S. epidermis used in the described experiments are the only ones tested to date (due to safety issues) and are not the ones known to be fully resistant (MRSE or MRSA). However, they are derivatives of those bacteria and show no response (resistance) to methicillin introduced without nanotubes in 2 out of 3 tests conveyed. Thus, nanotubes help overcome that antibiotic resistance.

Additional objects, features and advantages will be apparent in the written description which follows.

BRIEF DESCRIPTION OF THE DRAWINGS

FIG. 1(a) is a graph illustrating inhibition zones arising from individual components (SWCNT/DSPE-PEG 5000, Doxycycline, Methicillin) and SWCNT/antibiotic hybrids at two different concentrations;

FIG. 2(a) is a graph showing ANOVA and Dunnet's method statistical analysis of doxycycline disk diffusion data for 0.5 mg SWCNT, 2 mg antibiotic loaded;

DETAILED DESCRIPTION OF THE INVENTION

Figure 1B:
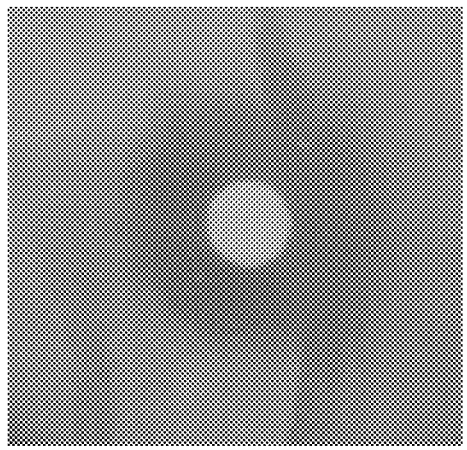
FIG. 1(b) is an image of an inhibition zone of S. epidermidis treated with Doxycycline.
Figure 1C:
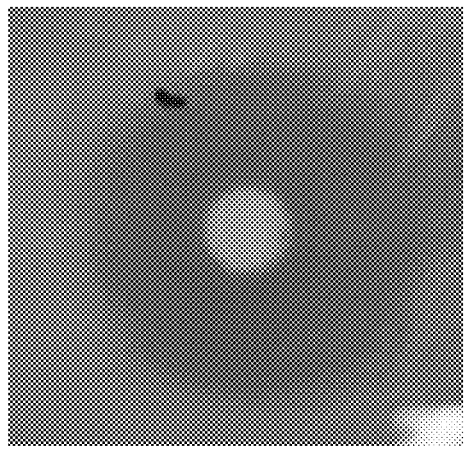
FIG. 1(c) is an image of an inhibition zone of S. epidermidis treated with SWCNT/Doxycycline.
Figure 1D:
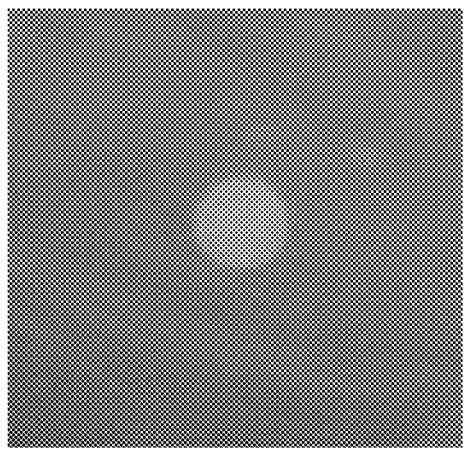
FIG. 1(d) is an image of an inhibition zones of S. epidermidis treated with Methicillin.
Figure 1E:
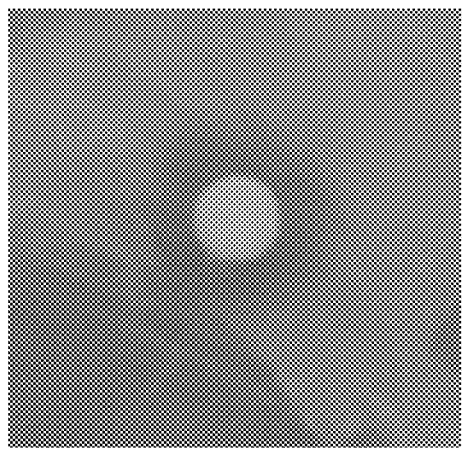
FIG. 1(e) is an image of an inhibition zone of S. epidermidis treated with SWCNT/Methicillin.

As discussed in the Background of the invention, due to the misuse and overuse of conventional antibiotics, resistant infections are on the rise. Those include well-known bacterial strains such as Staphylococcus aureus (MRSA) infection, Streptococcus pneumoniae, and Mycobacterium tuberculosis. It is predicted that approximately 10 million people will die from resistant infections by the year 2050 alone, not considering the emergence of new mutated strains. This mortality prediction exceeds that of cancer and diabetes combined. In response to such a daunting crisis, the scientific community has been developing new antibiotics. However that approach is hardly sustainable and not long lived, rather, giving rise to multi-drug resistant infections such as MRSA and VRCE. With mutated bacterial infections being the foundation for many large-scale health issues including M. tuberculosis, MRSA and VRE, the crisis of antibiotic resistance becomes a global threat.

To date very few routes were explored to address the antibiotic resistance including the inhibition of mutation, change in dosing regimen of existing antibiotics and delivery-assisted combination treatments. However dosing strategies provide only temporary solution that delay the formation of resistance, and inhibitory approaches have to be applied to bacteria prior to mutation that renders antibiotics ineffective. With the few successful delivery-assisted attempts to address the existing antibiotic resistance, current studies still focus more on the development of new antibacterial strategies. In the systems and techniques of the present invention, an alternative multimodal approach to the issue at hand is explored. Rather than developing an entirely new treatment, this work the first time proposes non-covalently formulating existing antibiotics with single-walled carbon nanotubes (SWCNTs) for delivery, imaging and enhanced antibiotic efficacy. SWCNTs provide a new multifunctional route to antibiotic delivery with concomitant capability of fluorescence-based tracking of transported therapeutics.

For the context of the studies which follow, the SWCNT-antibiotic dispersions are tested against Staphylococcus epidermidis. Because of the increased use of biomaterials in the hospital and clinical environment, S. epidermidis has become one of the five most common bacteria to cause nosocomial infections on prosthetic parts, valves, surgical wounds, urinary tract or bone marrow transplants. Once bacterial strains develop in these scenarios, it often difficult to treat them with antibiotics, forcing removal and replacement of the aforementioned tissues. While already causing nearly one million infections and many deaths per year, *S. epidermidis* has become resistant to a wide scope of antibiotics. Strains of *S. epidermidis* is resistant to methicillin, penicillin, penems, carbapanems, and cephalosporins. With these being the most commonly used antibiotics, an increase in *S. epidermidis* infections becomes a big threat.

SWCNTs offer great promise as antibiotic delivery vehicles due to their unique physical and optical properties. Known for their quasi-one-dimensional structure, SWCNTs have the dimensions suitable for cellular internalization show low cytotoxicity when formulated, accumulate partly in actin cytoskeleton but exhibit excretion over time. Additionally, a significant amount of SWCNTs can be loaded into a target cell, making them suitable for the delivery of hydrophobic drugs and gene therapies sensitive to degradation in blood. SWCNTs also show a potential for antibiotic delivery as multiple antibiotics are known to adsorb well on SWCNT surfaces and with covalent attachment improve the efficacy of ciprofloxacin antibiotic. The mechanism of SWCNT interaction with bacteria is so far unknown and can be further explored with molecular imaging. SWCNTs can be used for that purpose as efficient biomarkers since semiconducting species exhibit fluorescence in the near-infrared where biological autofluorescence background is minimal. SWCNT emission does not experience photobleaching, avoiding one of the drawbacks of conventional fluorophores, and can penetrate through the layers of biological tissue due to tow tissue absorption/scattering in near-IR. SWCNT-mediated fluorescence imaging can, therefore, be used to track the location of therapeutics in the targeted cells and tissues.

Despite these advances in SWCNT molecular imaging and initial work on antibiotic transport, the issue of antibiotic resistance still remains unsolved as there are no reports of SWCNTs recycling antibiotics to which the bacteria were previously resistant and no knowledge of the mechanism by which SWCNT delivery can address this resistance. Image-guided delivery of antibiotics allowing to track their transport and help elucidate SWCNT-guided mechanism of action has also not been explored to date as the covalent attachment of antibiotics is known to quench SWCNT emission.

The method of the present invention utilizes non-covalent SWCNT antibiotic delivery not only to enhance antibiotic efficacy and track the transport with intrinsic SWCNT fluorescence, but also to circumvent the antibiotic resistance of the bacteria previously showing resistant behavior. The focus is on overcoming the lack of antibiotic sensitivity of *S. epidermis* to methicillin. Also, antibiotic resistance is based partly on enzymatic degradation of the existing antibiotics or a decreased membrane permeability to those. Using SWCNTs as delivery vehicles, one aim of the present invention is to address both of these issues as they are known to protect delivered gene therapeutics from enzymatic degradation and enhance cellular internalization of other drug moieties. Additionally other research has identified the antibacterial properties of SWCNTs that may disrupt the membrane an for metabolic processes and morphology of bacteria. This all suggests that SWCNTs may be highly advantageous delivery vehicles for antibiotic treatment.

Due to their hydrophobic structure, in a number of biological applications, SWCNTs are dispersed via biocompatible surfactants including PEG or PEI derivatives. Although those mask SWCNTs in blood, yielding longer circulation times, additional dispersing agents increase the complexity of the formulation potentially hampering the release of the therapeutic. This work uses a unique antibiotic delivery method functionalizing SWCNTs non-covalently with antibiotics themselves allowing for SWCNT dispersion in aqueous media and antibiotic delivery directly on the SWCNT surface. Such non-covalent delivery also improves the possibility of antibiotic release within bacterial cells.

Using SWCNTs in combination with existing antibiotics provides a synergetic approach which, using the principles of the invention, yields not only successful delivery and imaging, but up to 70% improvement of the antibiotic efficacy for antibiotics to which bacteria showed resistant behavior. This may open a novel route for recycling existing antibiotics and effectively combating antibiotic resistance, the major issue in antibacterial treatment.

Methods 1.1 Dispersion of SWCNT in Antibiotic Solutions

Aqueous Doxycycline (20 mg/ml) and Methicillin (25 mg/ml) antibiotic solutions were used in this study to complex with SWCNT. Various SWCNT and antibiotic concentrations were tested to obtain an optimal concentration of SWCNTs of 500 µg dispersed in 1 mL of the corresponding antibiotic solution This yields the highest fluorescence efficiencies of ~1 representing the ratios of integral fluorescence to integral absorption assessed using Applied Nanofluorescence NS-2 Nanospectralyzer. Each antibiotic in aqueous solution was complexed with 500 µg of raw HiPco (Nanointegris batch # HR27-075A) non-covalently via 30 min of ultrasonic bath treatment followed by 20 min ultrasonic tip treatment at 3 W of power. SWCNT/antibiotic dispersions were centrifuged for 30 min at 16000×G to remove SWCNT aggregates. Resulting suspensions containing individual antibiotic-suspended SWCNTs were characterized via absorption spectroscopy and stored at 4° C. with further exposure to 2 min ultrasonic treatment prior to use.

For control experiments solution of SWCNTs/DSPE-PEG 5000 was prepared: 0.5 mg of SWCNT was added to a 1600 µM solution of DSPE-PEG 5000 (NanoCS) and subjected to the aforementioned ultrasonic dispersion and filtration procedures to yield final SWCNTs/DSPE-PEG 5000 suspensions.

1.2 Characterization of SWCNT-Antibiotic Dispersions

Concentration of all SWCNT suspensions were characterized via absorption spectroscopy. Using standard calibration curve constructed from absorptions of unfiltered SWCNT/antibiotic fractions with known SWCNT amounts we have experimentally derived extinction coefficients at 632 nm for SWCNT dispersed with both drugs (0.015 $(\mu g/mL)^{-1}$ for SWCNTs/doxycycline, and 0.0134 $(\mu g/mL)^{-1}$ for SWCNTs/methicillin). We further used those to assess the concentration of SWCNTs in centrifuged suspensions.

Concentration of antibiotic in the suspensions of antibiotic/SWCNT hybrids was assessed via deconvoluting absorption spectra of those into components for SWCNTs and antibiotic. SWCNTs/DSPE-PEG 5000 spectra were used as an assessment for SWCNT component and antibiotic standards at known concentrations were used as reference component for antibiotics. This calculation showed w/w ratios of 1:4 for SWCNT/methicillin and 1:5 and SWCNT/doxycycline in stock SWCNT suspensions that were further used throughout this work.

1.3 Disk Diffusion Assay

*S. epidermidis* broth of McFarland 0.5 standard (absorption of 0.08 to 0.1) was created using Mueller Hilton Broth. This standard stabilized the cell count at an approximate 1×10^8 CFU/mL Dilution was plated within 15 minutes of standardization. Following the proper aseptic techniques, 0.2 mL of bacterial broth was placed in the center of prepared agar dish. A sterile bacteria spreader was used to evenly spread the bacteria throughout the plate to create a lawn.

Two different dosages of the antibacterial solutions were tested to increase the breadth and reliability of data. Blank sensitivity discs were loaded with 10 μL and 20 μL (based on respective dosage) of stock suspensions and placed onto the surface of the agar using sterile forceps. Discs were impregnated with the test solution dropwise. Five discs were evenly placed equidistant from one another. Before tilting over the Petri dishes, discs were left to dry and gently pressed down to ensure attachment to agar. Once all Petri dishes are prepared, they were turned upside down to prevent surface condensation. Petri dishes are incubated for 24 h at 37° C., then the zones of inhibition were measured with the inclusion of disk diameter in the measurements.

1.4 Colony Count Assay

Using *S. epidermidis* broth (McFarland 0.5 standard), 100 μl was placed in the center of the agar plate. 100 μl of the respective antibacterial stock solution is added to the center. Bacteria was spread through the Petri dish and the plates were further incubated for 24 h at 37° C. Pictures of the plates were uploaded onto the OpenCFU software to count the number of colonies grown on the plate. Two plates were prepared for each antibacterial treatment with corresponding controls.

1.5 Turbidity Assay

A serial dilution (using the factor of 2) of antibacterial solutions was conducted in 12-well plates starting with 200 μL of antibacterial solution was placed in first well. 850 μl of broth and 50 μl of bacterial broth were added to each well plate. The concentrations tested for doxycycline were 1, 0.5, 0.25, 0.125 and 0 mg/mL. The concentrations tested for methicillin are 1.25, 0.625, 0.313, 0.106 and 0 mg/mL. Plates were that incubated at 37° C. for 24 h. The solutions were transferred to cuvettes, and their turbidity is measured using a Cary 500 spectrophotometer with the broth used as a baseline. Two wells were prepared for each concentration.

1.6 Cytotoxicity Assay

An MTT cytotoxicity assay was conducted for 4 samples: doxycycline, SWCNTs/doxycycline, methicillin, and SWCNTs/methicillin), Thiazolyl Blue Tetrazolium Bromide, and DMSO. Each sample was prepared via serial dilutions at the testing concentrations ranging from 0 to 3.5 μg/mL for doxycycline and SWCNTs dispersed with doxycycline and 0 to 0.25 μg/mL for methicillin and SWCNTs dispersed with methicillin. The absorbance is measured using the FLUOstar Omega microplate reader, and analyzed using Omega software.

1.7 Microscopy

We utilize InGaAs near-IR (NIR) camera coupled to hyperspectral fluorescence filter (Photon etc.) to perform fluorescence microscopy of SWCNTs imaged in bacterial cells 24 h after introducing to bacterial culture. The sample was excited with 637 nm diode laser excitation at 700 mW output power. SWCNTS showed up in the nIR broadband (900-1450 nm) images (FIG. 6) as bright fluorescent objects. Non-treatment control images were taken for each antibiotic target ensuring no emission in the near-IR. Scanning Electron Microscope (JEOL-JSM-7100F) was used at 5 kV to image bacterial cells deposited from the culture onto conductive carbon tape. SEM allowed imaging the outer surface of bacterial cells and extracellular SWCNTs.

Results & Discussion

2.1 Characterization

Noncovalently complexed SWCNT/antibiotic hybrids were prepared in this work for the first time. Antibiotics were utilized both as a payload and as surfactant for SWCNTs providing stable aqueous dispersions with fluorescence efficiencies remaining high (close to 1) for over a week. Doxycycline and methicillin were specifically chosen for this role due to characteristic hydrophobic regions in their structure some of which are expected to non-covalently bind to SWCNTs via π-stacking. While doxycycline is a tetracycline antibiotic and inhibits reproduction by disrupting protein synthesis, methicillin is a beta-lactam antibiotic that affects the bacteria by interfering with membrane structure. Using two antibiotics from different classifications allows for an understanding of how SWCNTs perform with different modes of action. Additionally, *S. epidermis* strain used in this work shows no/low response to methicillin suggesting some resistance and thus is intended as a control for the studies.

As SWCNTs alone are insoluble in water, their successful dispersion helps verify their complexation with antibiotics. Characteristic absorption spectra of SWCNTs and antibiotics were used to assess concentrations of those upon complexation. As absorption of both antibiotics is negligible in the visible, the value of absorption at 632 nm is used to determine the amount of SWCNTs (FIGS. 4(*a*) and (*b*)). A calibration curve constructed with known concentration of SWCNTs in unfiltered suspensions of SWCNT/antibiotic hybrids allows to determine extinction coefficients for SWCNT/doxycycline and SWCNT/methicillin absorption in die visible to be 0.015 $(\mu g/mL)^{-1}$ and 0.0134 $(\mu g/mL)^{-1}$ respectively. Antibiotic concentration in the final dispersion is assessed by deconvolving spectra of antibiotic/SWCNT hybrids via presenting those as a superposition of those of SWCNT and antibiotic alone at known concentrations, which resulted in the w/w ratios of ~1:4 for SWCNT/methicillin and ~1:5 and SWCNT/doxycycline aqueous suspensions.

2.2 Antibacterial Performance of SWCNT-Antibiotic Dispersions

Three different antibacterial sensitivity assays were used to verify the efficacy of SWCNT/antibiotic dispersions. The disk diffusion assay, colony formation assay and turbidity assay confirm the findings of the invention through three different procedures.

2.2.1 Zone Inhibition Assay

The antibacterial effects of pure antibiotic solutions are first compared to non-treatment control and vehicle control provided by SWCNT/PEG formulations. Here DSPE-PEG-5000 is used as a biocompatible dispersing agent for SWCNTs to provide stable aqueous dispersions without the use of antibiotics:

In this formulation SWCNTs show little to no antibacterial effect, which is supportive of their sole role as drug delivery/imaging agents providing no interference with antibacterial efficacy of the payload. Among the antibiotics, doxycycline is significantly more effective at both 2 and 4 mg doses, whereas methicillin shows no antibiotic activity with inhibition levels same to non-treatment control. Since strains of *S. epidermis* are known to show antibiotic resistance and several are specifically resistant to methicillin. The complete lack of inhibition response with this antibiotic for colony formation and disc diffusion assays likely indicates a resistant behavior of the current strain to methicillin. At the same time no resistance to doxycycline has been observed.

Concentrations of antibiotics in complexes with SWCNTs were further chosen to mimic those of unformulated antibiotics. SWCNT/antibiotic dispersions show substantial improvement in the inhibition response for both antibiotics. SWCNT/Doxycycline dispersion becomes slightly more effective than Doxycycline alone (8% improvement), whereas SWCNT/Methicillin hybrids exhibits a drastic improvement: an increase in efficacy from no observable bacterial inhibition to the 50% of the inhibition response of doxycycline. Because *S. epidermidis* in this test is initially resistant to methicillin, this increase in antibacterial efficacy signifies that SWCNT delivery is likely to bypass antibiotic resistance. While there are a number of theories regarding the mechanisms of cellular internalization of carbon nanotubes, many are proposing a more efficient entry due to interaction of hydrophobic SWCNT platform with membrane lipids. Depending on their surface properties, SWCNT may partially disrupt the membrane leading to its potation or potentially cause oxidative stress-mediated damage to bacterial membranes. These mechanisms of nanotube-membrane interaction at higher concentrations may lead to antibacterial effects. Thus, considering that methicillin's mechanism of action is based on the disruption of bacterial cell membranes it is plausible that SWCNT/membrane interaction may prevent the recognition of antibiotic by the resistant bacteria, and facilitate its delivery inside the membrane where methicillin may successfully perform its primary function.

2.2.2 Statistical Analysis

The statistical analysis performed in this work confirm the significance of the observed results for diffusion discs performed at different amounts of SWCNT/antibiotic complex loaded onto discs. Data analysis was performed using JMP software utilizing ANOVA (Analysis of Variance) to provide the statistical information to understand the predominant effects and significance of differences in data. In performing an ANOVA on a dataset, a null hypothesis was made, stating that the average means of the various treatments are the same. When the p-value of the analysis is lower than the confidence level chosen, the hypothesis is proven false and a significant difference and variation is detected.

The dataset is analyzed using a comparison of means function by assigning a mean of the control group and comparing it to the means of each of the treatment groups. The degree of overlap of the circles in the graphic represents their significant similarity or difference, whereas the size is proportional to the corresponding variance.

Figure 2B:
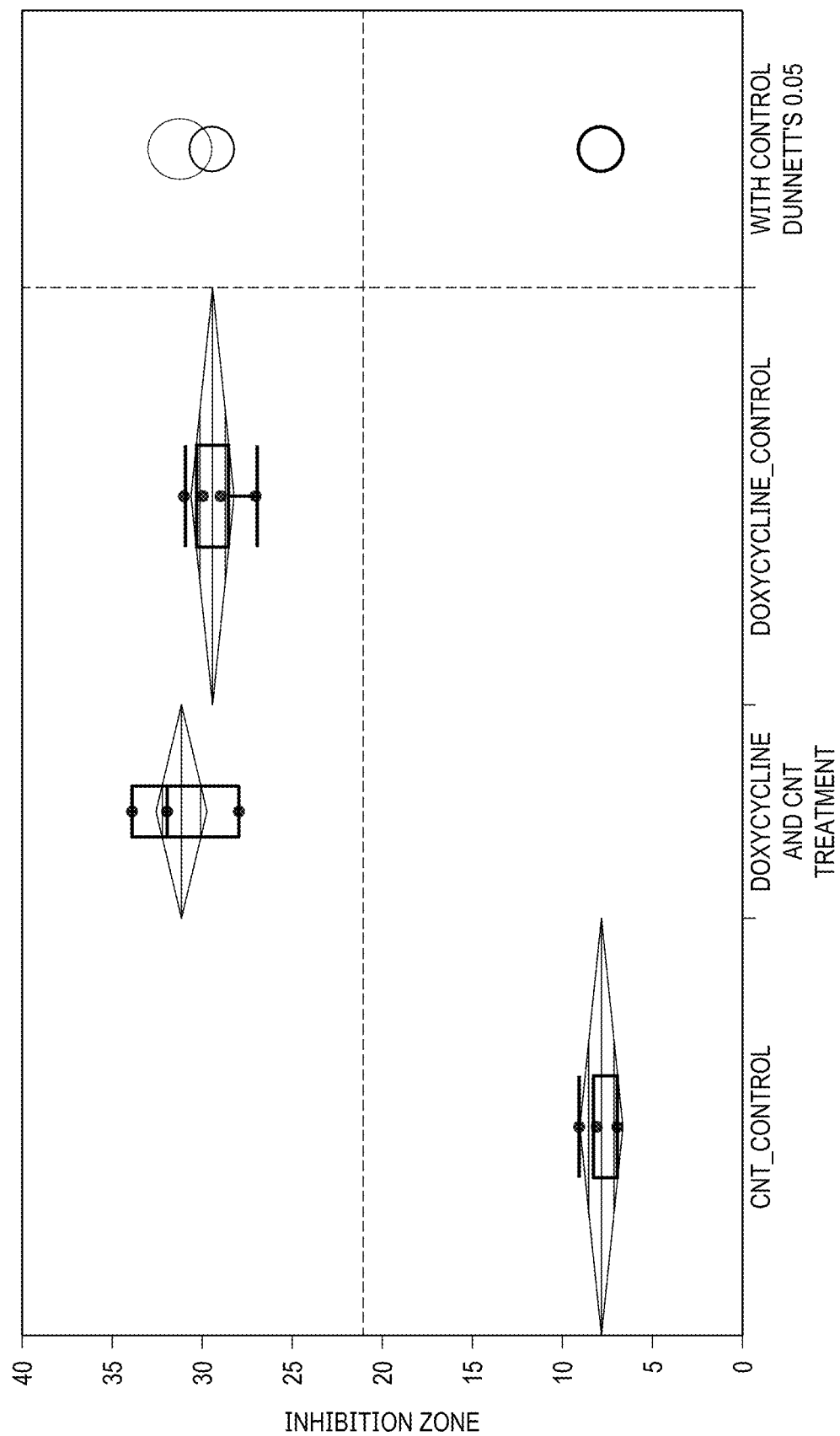
FIG. 2(b) is a graph showing ANOVA and Dunnet's method statistical analysis of doxycycline disk diffusion data for 1 mg SWCNT, 4 mg antibiotic loaded.
Figure 2C:
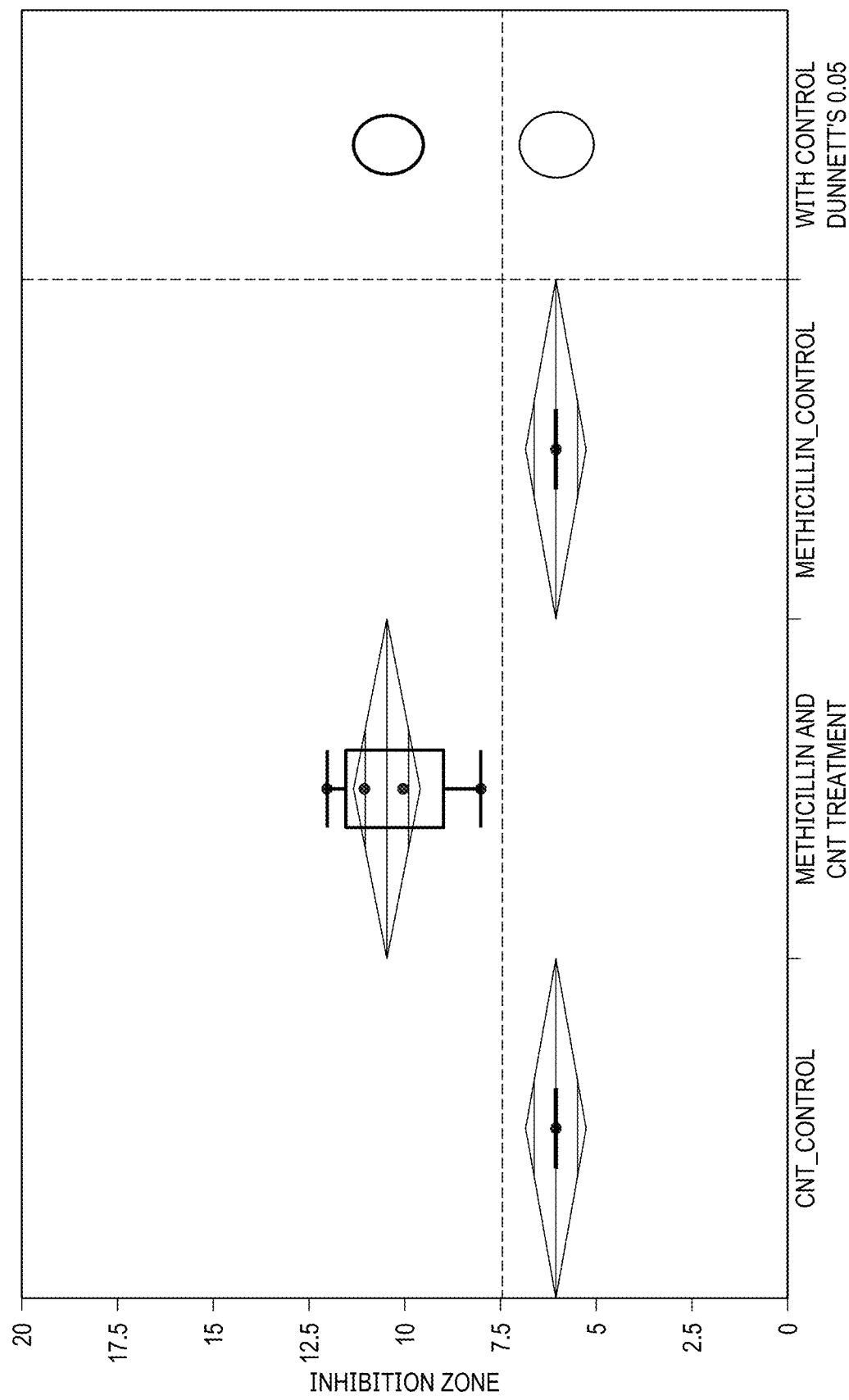
FIG. 2(c) is a graph showing ANOVA and Dunnet's method statistical analysis of methicillin disk diffusion data for 0.5 mg SWCNT, 2.5 mg antibiotic loaded.
Figure 2D:
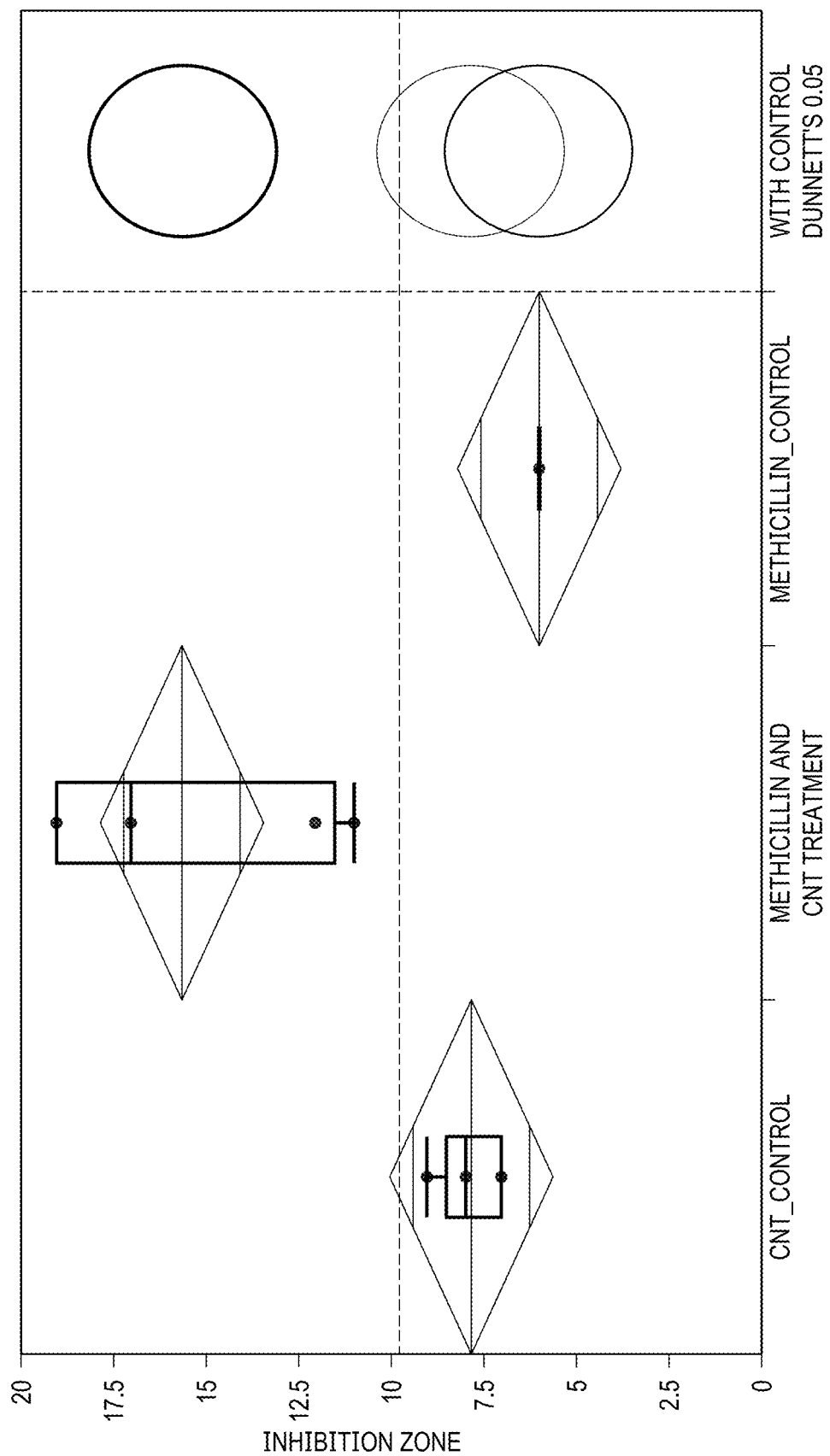
FIG. 2(d) is a graph showing ANOVA and Dunnet's method statistical analysis of methicillin disk diffusion data for 1 mg SWCNT, 5 mg antibiotic loaded.

For comparison of antibiotic effects of SWCNT/Doxycycline to the free antibiotic (FIG. 2(*a*), (*b*)), the differences in data are significant. For both dosages of doxycycline the R-square is fairly high (~0.97), and the Prob>F is low (<0.0001), indicating a considerably good fit of the data. Based on the Control Dunnett's method, the difference between the control (antibiotic alone) and SWCNT/antibiotic hybrids is insignificant for 2 mg dosage, but is considered significant for 4 mg dosage. Overall, it can be inferred that the complexes of SWCNT/doxycycline exhibit marginally better activity than antibiotic alone. Unlike in the case of doxycycline, statistical analysis shows a significant improvement in antibacterial efficacy for SWCNT/methicillin hybrids. R-squares are relatively high (~0.9 and 0.8) and prob>F are low (<0.0001), indicating a good fit of the data. The Control Dunnet's circles for both doses (FIGS. 2(*b*),(*c*)) show that the difference between control and treatment is significant and SWCNT/methicillin complex is statistically much more efficacious than methicillin alone.

Figure 3D:
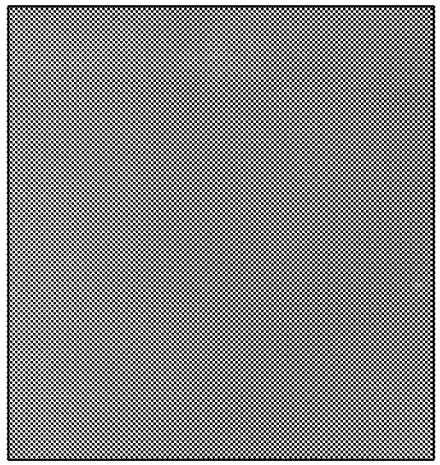
FIG. 3(d) shows the S. epidermidis treated with Doxycycline-SWCNT dispersion.
Figure 3C:
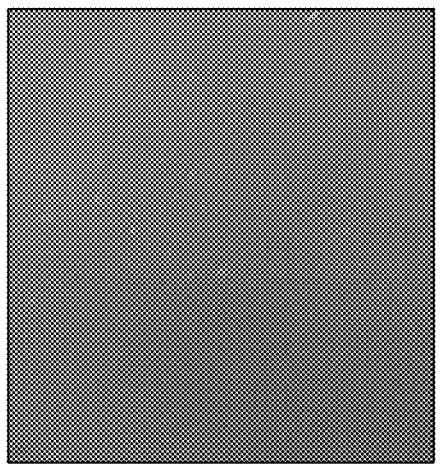
FIG. 3(c) shows the S. epidermidis treated with Doxycycline.
Figure 3B:
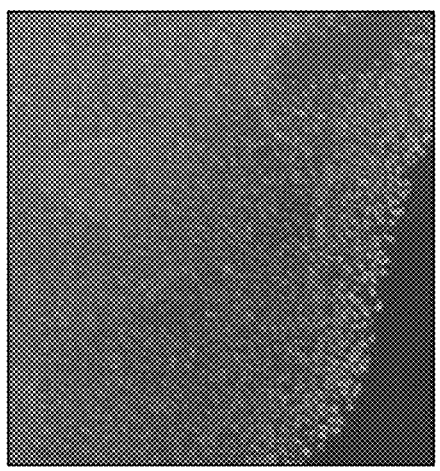
FIG. 3(b) is the S. epidermidis control.
Figure 3F:
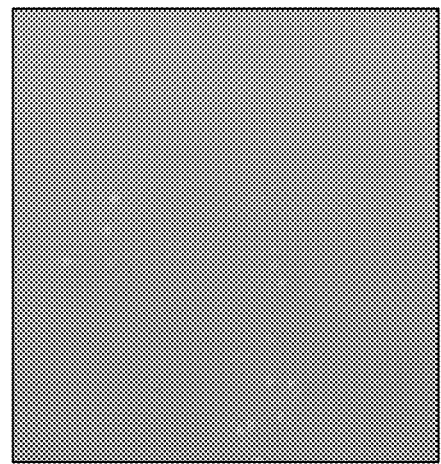
FIG. 3(a) is a graph of Colony Formation Unit assay of antibiotics and antibiotic-SWCNT dispersion. Colonies on each plate counted with OpenCFU software.
FIG. 3(e) shows the S. epidermidis treated with Methicillin.
FIG. 3 (f) shows the S. epidermidis treated with Methicillin-SWCNT dispersion.
Figure 3E:
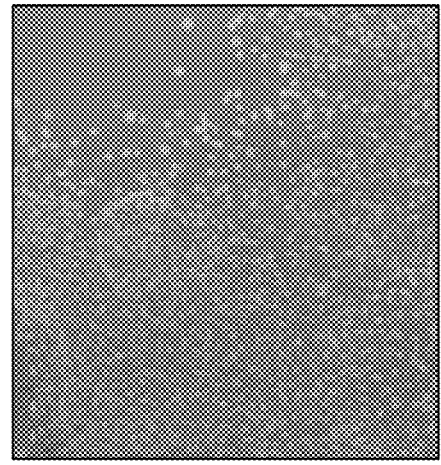

The results from the colony formation assay support that the efficacy of SWCNT/antibiotic hybrids is greater than that of the antibiotics alone. SWCNT/Doxycycline formulation provides slightly lower colony counts than the antibiotic alone with 68% improvement both being highly effective against *S. epidermis*. The colony count for methicillin alone is similar to the control, as expected, whereas that for SWCNTs/methicillin is suppressed 40-fold (4000% improvement) showing significant observable (FIG. 3*f*) decrease in the number of colonies. Such drastic increase in efficacy for SWCNT-delivered methicillin with corresponding only minor improvement for already effective doxycycline can be likely attributed to bypassing of antibiotic resistance via SWCNT delivery.

Figure 4A:
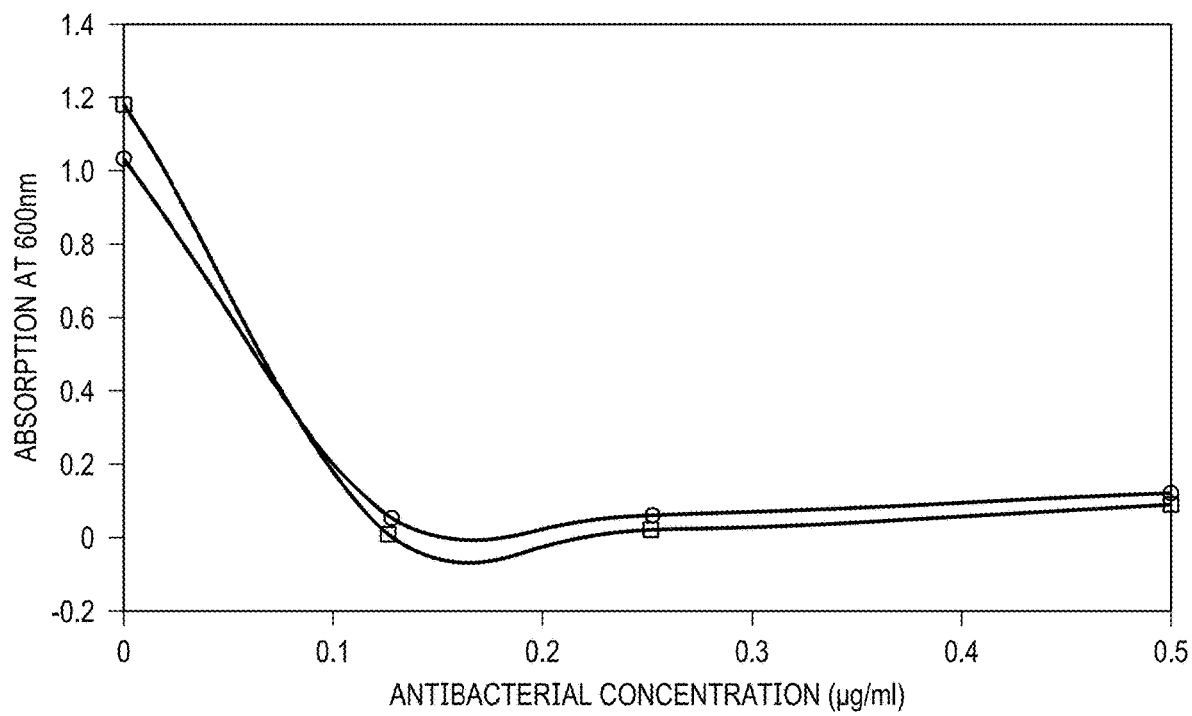
FIG. 4(a) is a graph of showing turbidity assay absorption data at 600 m for Doxycycline and SWCNT/Doxycycline.
Figure 4B:
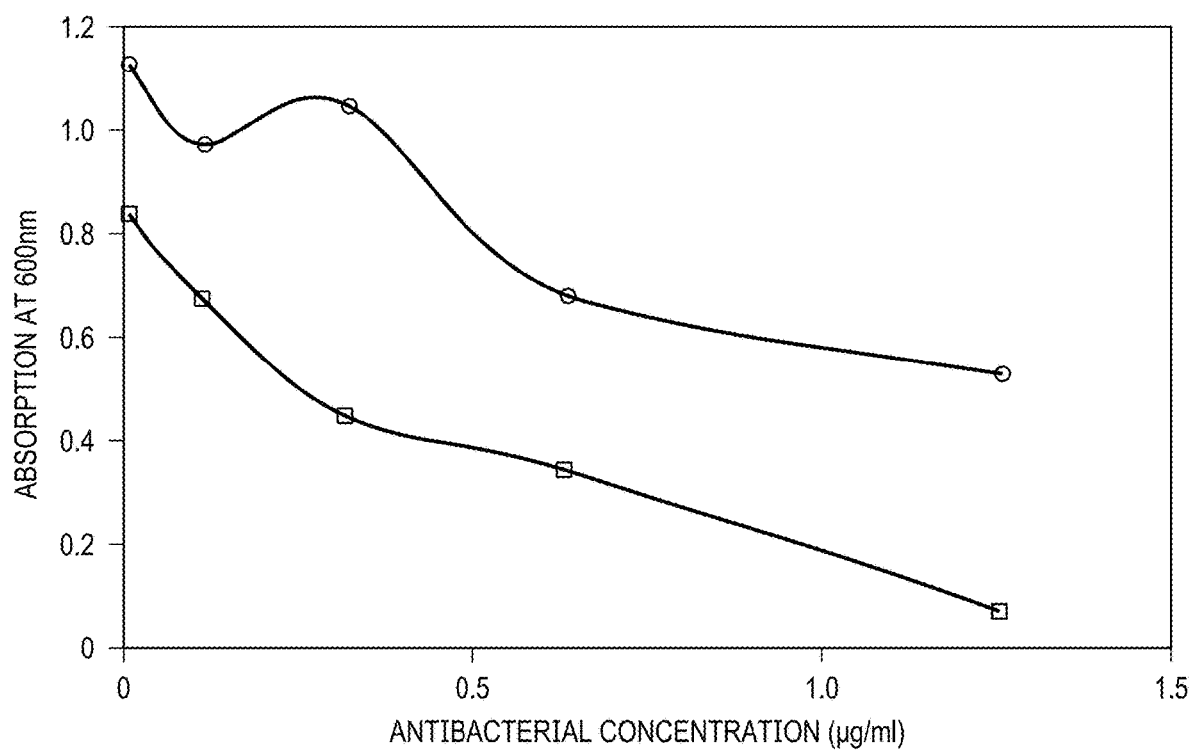
FIG. 4(b) is a graph showing turbidity assay absorption data at 600 m for Methicillin and SWCNT/Methicillin.

The turbidity assay performed with SWCNT/antibiotic formulations in bacterial media assessed scattering from turbid samples proportional to bacterial concentration in suspension. Relative scattering is assessed by the magnitude of scattering background in absorption spectra sampled at 600 nm. Due to the low concentrations of antibiotics and SWCNT used in this study, SWCNT absorption does not interfere with turbidity measurements. The absorption data in FIGS. 4*a* and 4*b* is therefore presented as a Minimum Inhibitory Concentration Test. Rather than using a MIC value however, the overall turbidity curve is utilized to assess the amount of bacteria remaining in the respective suspensions. As consistent with findings of two previous methods, bacteria treated with SWCNT/methicillin complexes exhibit a lower turbidity than the same doses of methicillin alone. Although antibiotic control for this test shows some bacterial inhibition, a significant improvement upon SWCNT complexation is noted. Doxycycline/SWCNTs hybrids yield slightly lower turbidity in bacterial media as opposed to antibiotic alone as opposed to significant improvement for Methicillin.

As seen in all of the bacterial sensitivity assays, the complexation of antibiotics with SWCNTs increases the efficacy of the treatment when compared to antibiotic alone. SWCNT in this role may act as efficient drug carriers or, potentially, enhance effect of antibiotics in a combination treatment. While the improvement of doxycycline efficacy via the dispersion with SWCNTs is minimal, SWCNT/Methicillin complexes become far more efficacious bypassing the antibiotic resistance to methicillin.

2.4 Cytotoxicity

Figure 5A:
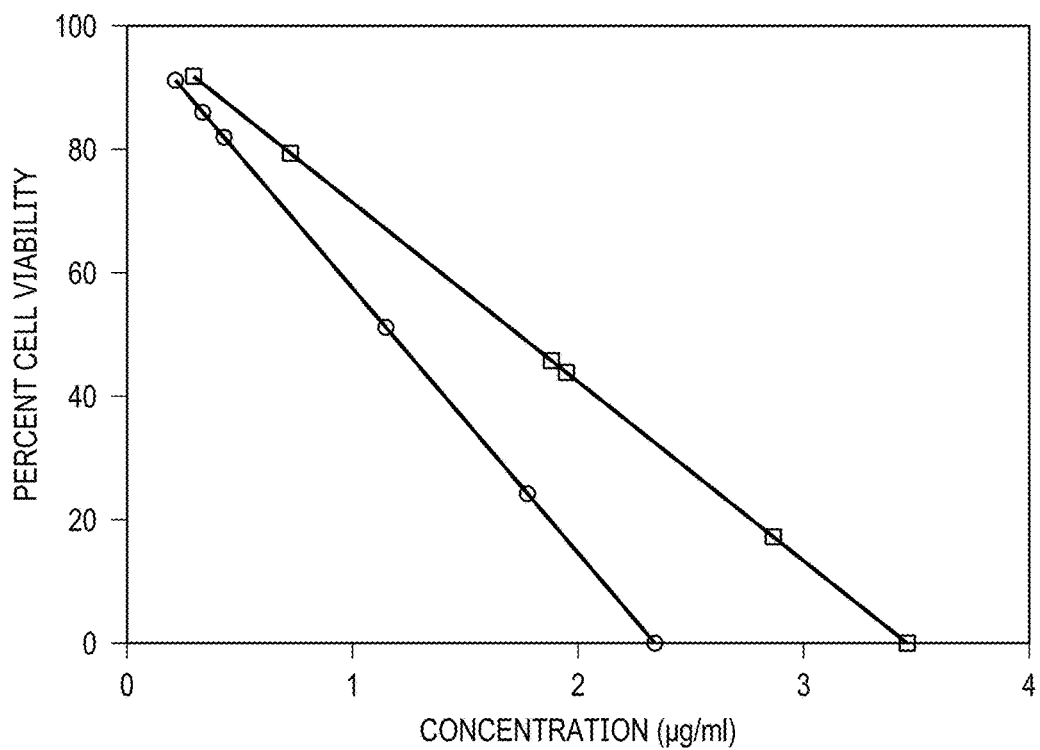
FIG. 5(a) is a graph of Cytotoxicity assay in HeLa cells comparing response to Doxycycline vs SWCNT/Doxycycline.
Figure 5B:
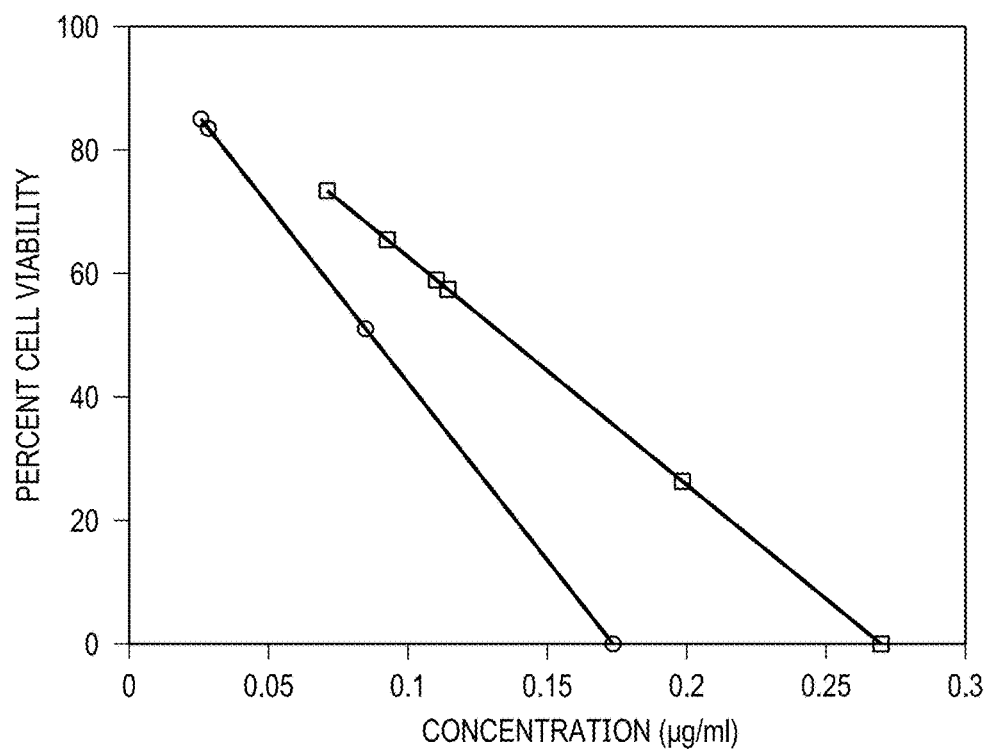
FIG. 5(b) is a graph of Cytotoxicity assay in HeLa cells comparing response to Methicillin vs SWCNT/Methicillin.
Figure 6A:
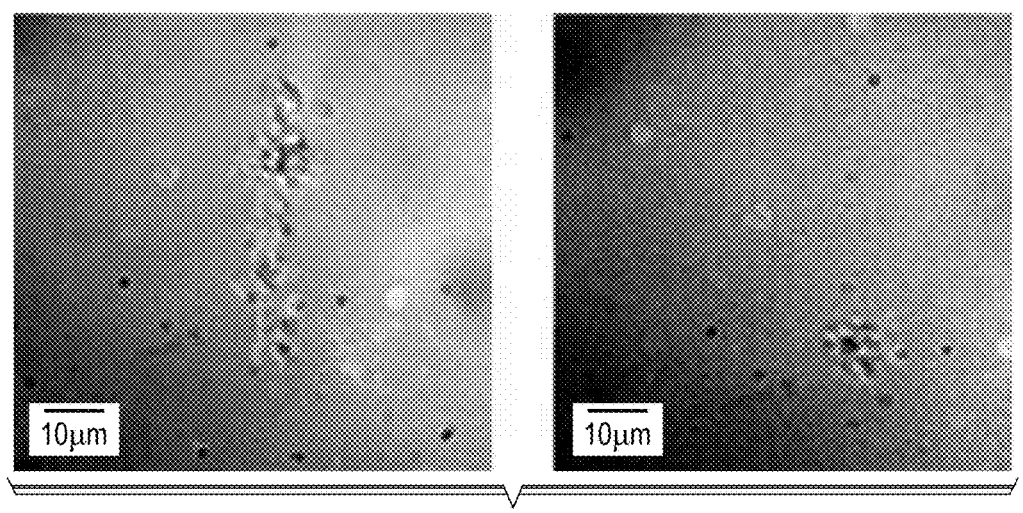
FIG. 6(a) shows the NIR Fluorescence imaging of SWCNT emission in bacterial cells subject to SWCNT/Methicillin treatment.
Figure 6B:
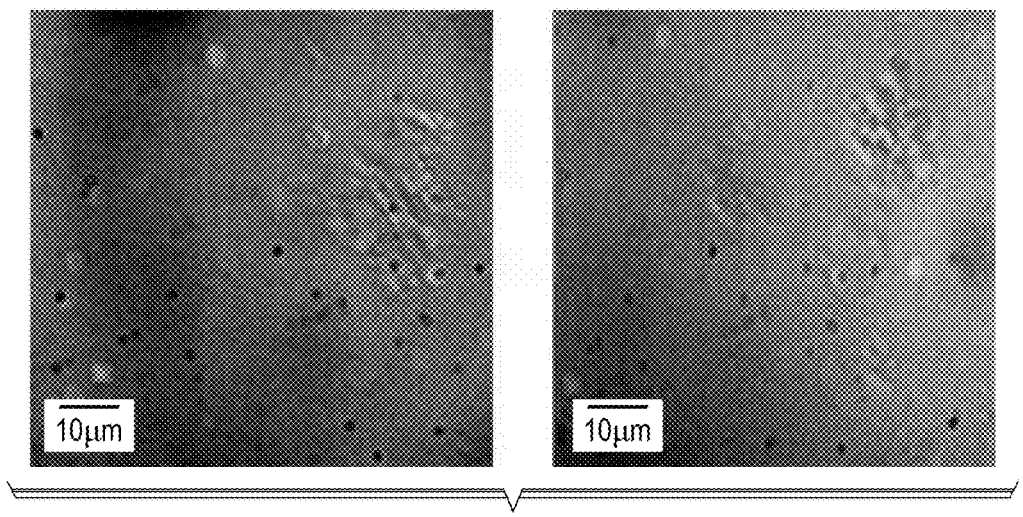
FIG. 6(b) shows the NIR Fluorescence imaging of SWCNT emission in bacterial cells subject to SWCNT/Doxycycline treatment.
Figure 6C:
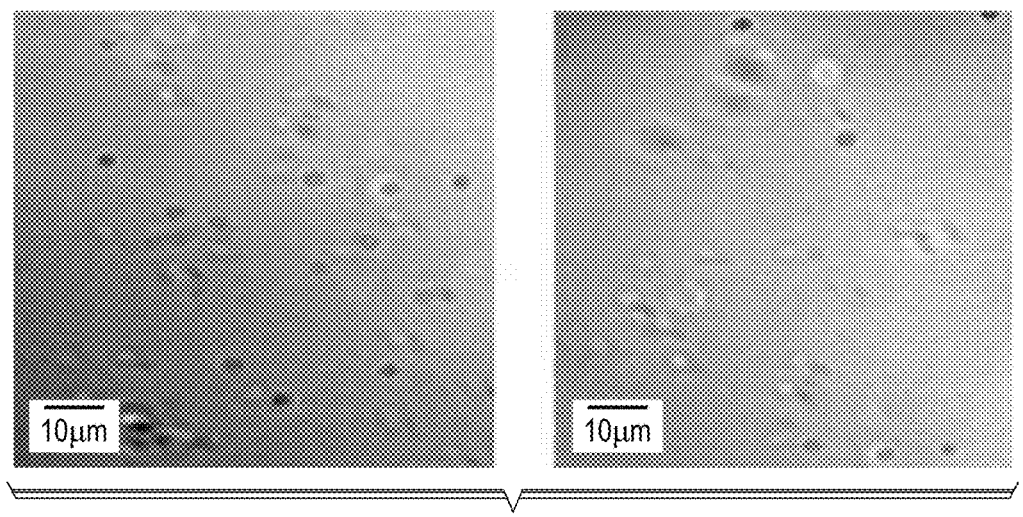
FIG. 6(c) shows the NIR Fluorescence imaging of SWCNT emission in bacterial cells subject to Non-treatment control.
Figure 6D:
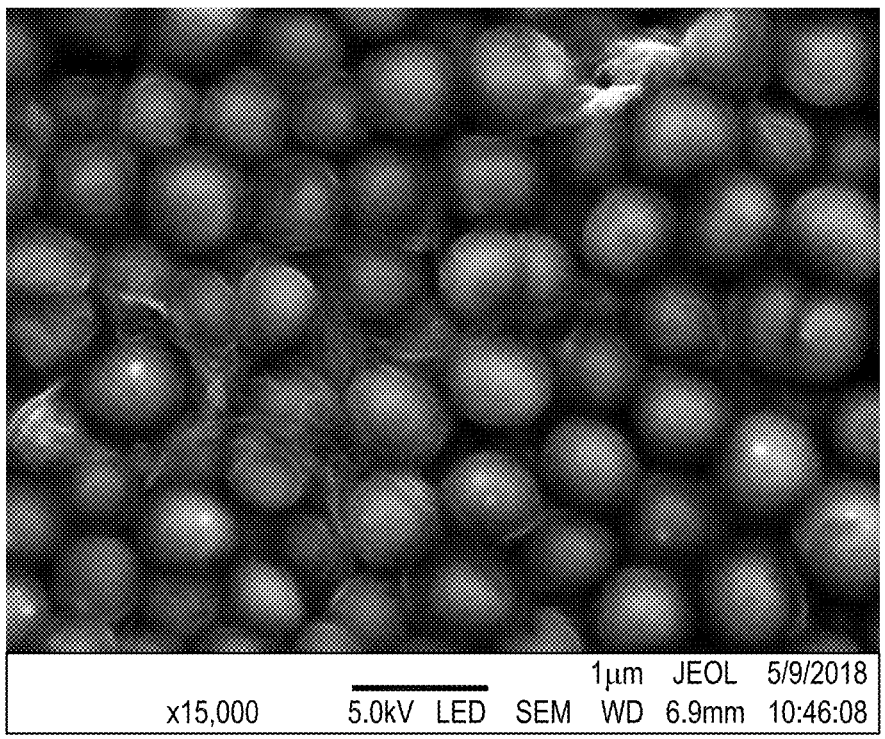
FIGS. 6(d) and 6(e) are SEM images of bacterial cells subject to SWCNT/methicillin hybrids.
Figure 6E:
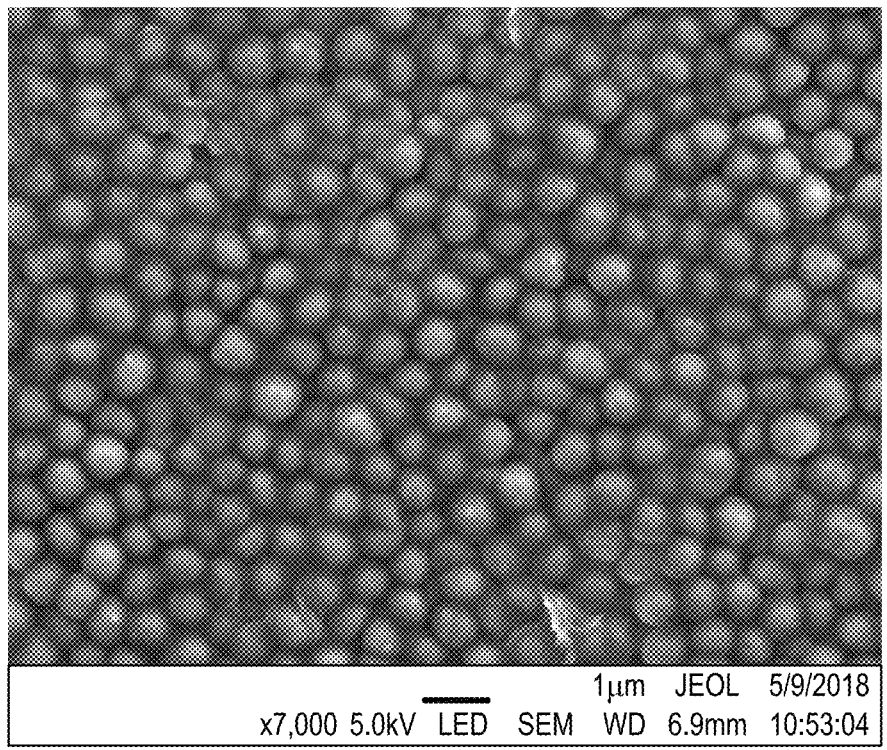

The observed effect was verified as not being due to inherent SWCNT toxicity in complexation with methicillin by a separate MTT cytotoxicity assay in HeLa cells (FIG. 5). For both Doxycycline and Methicillin SWCNT/antibiotic complexes at the same antibiotic dose show less inherent toxicity to HeLa cells than antibiotics alone indicating no toxic effect from SWCNTs.

2.5 Imaging

The inherent emission of SWCNTs in the near-IR was utilized to track and image those in bacterial cells collected from bacterial culture around the discs in the disc diffusion assay to verify cell internalization. Control bacteria were imaged together with the ones subject to SWCNT/methicillin and SWCNT/doxycycline treatments loaded on the discs. As biological autofluorescence background is minimal in the near-IR, we expect SWCNTs to be the major emissive species. In accordance with this, control cells show no observable emission whereas microscopy images of bacterial cells recovered in the vicinity of the discs with SWCNTs/methicillin and SWCNTs/doxycycline show bright near-IR SWCNT emission in the clusters bacterial cells. The highest signal intensities were found surrounding cells or cell clusters suggesting possible incorporation into the membrane. Extracellular SWCNT emission appears to be rare indicating preferential interaction of SWCNT/antibiotic hybrids with bacteria.

Considering resolution limitations of fluorescence imaging of small micrometer-sized bacterial cells, these findings were confirmed by the higher resolution SEM imaging of bacteria subject to SWCNT/methicillin hybrids. In SEM images showing the outer surface of the bacteria SWCNT are clearly observed associating with the membrane of bacterial cells in large quantities with some incidences of membrane penetration caught in the image. This preferential accumulation is likely to result in the enhanced antibiotic effect observed with SWCNT/doxycycline hybrids as its mechanism of action through inhibiting bacterial protein synthesis may be positively affected by the amount of the drug. As for methicillin, SWCNT-assisted penetration into cell membrane may aid the antibiotic to bypass the need to bind to PBP membrane receptors. S. Epidermis as well other strains expressing mutated form of PBP2 with lower binding affinity and increased release rates which suppresses methicillin membrane attachment and thus inhibits its efficacy.

Experimental results observed here suggest that SWCNTs acting as delivery vehicles with no inherent antibacterial activity provide an alternative route to membrane localization.

3. Conclusion

This work for the first time explores the joint delivery and imaging of antibiotics by single-walled carbon nanotubes. SWCNTs dispersed in water with doxycycline and methicillin non-covalently attached to their surface act as drug delivery vehicles facilitating the improved antibacterial effect in *Staphylococcus epidermidis*. In three different sensitivity assays performed in this work, the advantages of a SWCNT/antibiotic therapy are apparent. SWCNTs facilitate preferential bacterial accumulation of the payload and improved antibacterial effect for antibiotics of two different classes. A relative improvement with respect to antibiotic treatment alone varied from 68% increase in bacterial colony inhibition observed for SWCNT/doxycycline hybrids to 40-fold (4000%) improvement in bacterial colony inhibition for SWCNT complex with methicillin, to which *S. epidermidis* initially shows resistant behavior in our assays. These results confirmed by statistically significant findings from disc diffusion and a general trend provided by the turbidity assays suggest that whereas for doxycycline enhanced efficacy can be explained by increased uptake facilitated by SWCNT delivery; SWCN/methicillin complexes are likely bypass the antibiotic resistance of *S. epidermidis*. Based on the reported interaction of SWCNTs with cellular membrane, direct transport of the antibiotic into the membrane affected by SWCNTs appears to occur where methicillin's mechanism of action becomes effective or masking its recognition via SWCNT delivery. These hypotheses are supported by SWCNT fluorescence imaging within bacterial cell culture subject to SWCNT/antibiotic treatment indicating substantial SWCNT fluorescence signal originating from bacteria rather than extracellular environment. SEM images confirm the association of SWCNTs with the membrane of bacteria.

In this work SWCNT act as effective multifunctional antibiotic delivery/imaging agents with the potential to bypass antibiotic resistance. As methicillin is one of the more widely known antibiotics for developing resistance, its activation through noncovalent hybridization with SWCNTs offers an alternative potential approach to the antibiotic resistance crisis. It may further provide a chance to reduce the dose, reuse and recycle the existing antibiotics for the treatment of the new resistant bacterial epidemics.

While the invention has been shown in several of its forms, it is not thus limited but is susceptible to various changes and modifications without departing from the spirit thereof.

What is claimed is:

1. A delivery device for delivering a selected antibiotic drug to an antibiotic-resistant bacterial cell, the device comprising:
   a substrate for the antibiotic, the substrate comprising a single-walled carbon nanotube having a nanotube surface;
   wherein the selected antibiotic drug is complexed to the substrate by non-covalently bonding the antibiotic drug to the nanotube surface through adsorption of the antibiotic onto the nanotube surface, the bonding being governed by sufficiently strong molecular attraction between hydrophobic systems of antibiotic drug and the carbon nanotube;
   wherein the antibiotic is selected from the group consisting of doxycycline and methicillin.

2. The device of claim 1, wherein the single-mulled carbon nanotubes are dispersed in water with a selected one of the doxycycline and methicillin so that the selected antibiotic drug is non-covalently attached to the nanotube surface.

3. The device of claim 1, wherein the delivery device is effective in delivering an antibiotic drug which achieves an improved antibacterial effect against *Staphylococcus epidermidis*.

4. A method for delivering a selected antibiotic drug to a human body using nanotube for the therapeutic purpose of treating a bacterial infection, the method comprising the steps of:
   providing a single-walled carbon nanotube having a nanotube surface as a substrate for the selected antibiotic drug;
   wherein the selected antibiotic drug is complexed to the substrate to form a nanotube/drug hybrid by non-covalently bonding the antibiotic drug to the nanotube surface through adsorption of the antibiotic onto the nanotube surface, the bonding being governed by sufficiently strong molecular attraction between hydrophobic systems of antibiotic drug and the carbon nanotube; and administering the nanotube/drug hybrid;

wherein the antibiotic is delivered to a bacterial cell wherein the bacterial cell is an antibiotic resistant bacterial cell.

5. The method of claim 4, wherein the antibiotic drug, is selected from the group consisting of doxycycline and methicillin.

6. The method of claim 4, wherein the single-walled carbon nanotubes are dispersed in water with a selected one of the doxycycline and methicillin so that the selected antibiotic drug is non-covalently attached to the nanotube surface.

7. The method of claim 4, wherein the delivery device is effective in delivering an antibiotic drug, which achieves an improved antibacterial effect against *Staphylococcus epidermidis*.

8. The method of claim 4, wherein the method is used for cellular internalization of the selected antibiotic and acts, as a method for circumventing bacterial resistance to the selected drug.

9. The method of claim 4, further comprising the steps of;

visualizing the single-walled carbon nanotube fluorescence imaging inside the bacterial cells;

using the fluorescence imaging data as an imaging tool to track drug delivery.

\* \* \* \* \*